United States Patent
de Lera Ruiz et al.

(10) Patent No.: US 7,531,660 B2
(45) Date of Patent: May 12, 2009

(54) 1-[[1-[(2-AMINO-6-METHYL-4-PYRIDINYL)METHYL]-4-FLUORO-4-PIPERIDINYL]CARBONYL]-4-[2-(2-PYRIDINYL)-3H-IMIDAZO[4,5-B]PYRIDIN-3-YL]PIPERIDINE AND METHODS OF USE THEREOF

(75) Inventors: Manuel de Lera Ruiz, Branchburg, NJ (US); Robert G. Aslanian, Rockaway, NJ (US); Michael Y. Berlin, Flemington, NJ (US); Kevin D. McCormick, Basking Ridge, NJ (US); Chander S. Celly, Colonia, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/837,248

(22) Filed: Aug. 10, 2007

(65) Prior Publication Data

US 2008/0058370 A1 Mar. 6, 2008

Related U.S. Application Data

(62) Division of application No. 11/523,489, filed on Sep. 19, 2006, now Pat. No. 7,332,604.

(60) Provisional application No. 60/718,673, filed on Sep. 20, 2005.

(51) Int. Cl.
C07D 498/02 (2006.01)
A01N 43/42 (2006.01)

(52) U.S. Cl. ..................... 546/118; 514/303

(58) Field of Classification Search ............... 546/118; 514/303

See application file for complete search history.

(56) References Cited

U.S. PATENT DOCUMENTS

| | | | |
|---|---|---|---|
| 6,720,328 B2 | 4/2004 | Aslanian et al. | |
| 6,849,621 B2 | 2/2005 | Rosenblum et al. | |
| 7,332,604 B2 * | 2/2008 | de Lera Ruiz et al. | 546/118 |
| 2004/0019099 A1 | 1/2004 | Aslanian et al. | |
| 2004/0048843 A1 | 3/2004 | Ting et al. | |
| 2004/0097483 A1 | 5/2004 | Zeng et al. | |
| 2004/0224953 A1 | 11/2004 | Cowart et al. | |

FOREIGN PATENT DOCUMENTS

| | | |
|---|---|---|
| WO | WO 03/088967 A1 | 10/2003 |
| WO | WO 2004/089373 A1 | 10/2004 |
| WO | WO 2004/101546 A1 | 11/2004 |

OTHER PUBLICATIONS

Leurs, Rob, et al., "The Histamine H3 Receptor: From Gene Cloning to H3 Receptor Drugs", Nature Reviews, Drug Discovery (4):107-120, (2005).

Tashiro, Manabu, et al., "Roles of histamine in regulation of arousal and cognition: functional neuroimaging of histamine H1 receptors in human brain", Life Sciences 72:409-414 (2002).

PCT International Search Report dated Dec. 6, 2006 for corresponding PCT Application No. PCT/US2006/036424.

* cited by examiner

Primary Examiner—D. Margaret Seaman
Assistant Examiner—Nizal S Chandrakumar
(74) Attorney, Agent, or Firm—Jeffrey P. Bergman

(57) ABSTRACT

The present invention discloses the compound of Formula I

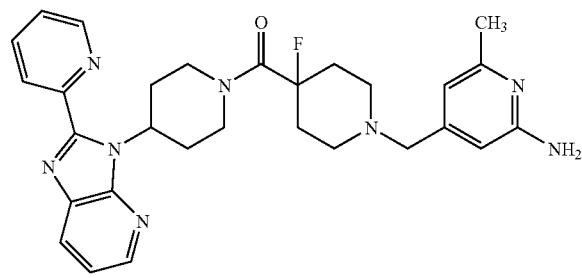

and pharmaceutically acceptable salts and solvates thereof. The invention also relates to pharmaceutical compositions comprising the Compound of Formula I and its use in treating obesity, metabolic syndrome, diabetes, hepatic lipidosis or nonalcoholic fatty liver disease. The invention also relates to the use of a combination of the Compound of Formula I with additional therapeutic agents for treating obesity, metabolic syndrome, diabetes, hepatic lipidosis or nonalcoholic fatty liver disease.

2 Claims, 1 Drawing Sheet

1-[[1-[(2-AMINO-6-METHYL-4-PYRIDINYL) METHYL]-4-FLUORO-4-PIPERIDINYL] CARBONYL]-4-[2-(2-PYRIDINYL)-3H-IMIDAZO[4,5-B]PYRIDIN-3-YL]PIPERIDINE AND METHODS OF USE THEREOF

RELATED APPLICATIONS

This application is a division of U.S. patent. application Ser. No. 11/523,489, filed Sep. 19, 2006, now allowed and herein incorporated by reference, which in turn claims benefit under 35 USC 119(e) to U.S. Provisional Patent Application No. 60/718,673, filed Sep. 20, 2005.

FIELD OF THE INVENTION

The present invention relates to 1-[[1-[(2-amino-6-methyl-4-pyridinyl)methyl]-4-fluoro-4-piperidinyl]carbonyl]-4-[2-(2-pyridinyl)-3H-imidazo[4,5-b]pyridin-3-yl]piperidine, a compound useful as a histamine $H_3$ antagonist. The invention also relates to pharmaceutical compositions comprising said compound and its use in treating obesity, metabolic syndrome, diabetes, hepatic lipidosis or nonalcoholic fatty liver disease. The invention also relates to the use of a combination of the histamine $H_3$ antagonist of this invention with other actives useful for treating obesity, metabolic syndrome, diabetes, hepatic lipidosis or nonalcoholic fatty liver disease. The use of the pharmaceutical compositions comprising the compound of the invention with one or more compounds for treating obesity, metabolic syndrome, diabetes, hepatic lipidosis or nonalcoholic fatty liver disease are also contemplated.

BACKGROUND OF THE INVENTION

The histamine receptors, $H_1$, $H_2$, $H_3$ and $H_4$ have been characterized by their pharmacological behavior. The $H_1$ receptors are those that mediate the response antagonized by conventional antihistamines. $H_1$ receptors are present, for example, in the ileum, the skin, and the bronchial smooth muscle of humans and other mammals. The most prominent $H_2$ receptor-mediated responses are the secretion of gastric acid in mammals and the chronotropic effect in isolated mammalian atria. $H_4$ receptors are expressed primarily on eosinophils and mast cells and have been shown to be involved in the chemotaxis of both cell types.

In the periphery, $H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation. In addition, in rodents, peripheral $H_3$ receptors are expressed in brown adipose tissue, suggesting that they may be involved in thermogenesis regulation.

$H_3$ receptors are also present in the CNS. $H_3$ receptor expression is observed in cerebral cortex, hippocampal formation, hypothalamus and other parts of the human and animal brain. $H_3$ receptors are expressed on histaminergic neurons and, as heteroreceptors, on neurons involved in other neurotransmitter systems, where $H_3$ receptor activation results in presynaptic inhibition of neurotransmitter release. In the particular case of histaminergic neurons, $H_3$ receptors have been implicated in the regulation of histamine hypothalamic tone, which in turn has been associated with the modulation of sleeping, feeding and cognitive processes in the human brain (see, for example, Leurs et al., *Nature Reviews, Drug Discovery*, 4, (2005), 107).

It is also known and has been described in the literature that histamine is involved in regulation of cognitive and memory processes in the human brain (see, for example, *Life Sciences*, 72, (2002), 409-414). Consequently, indirect modulation of histaminergic brain function through the central $H_3$ receptors may be a means to modulate these processes. Different classes of $H_3$ receptor ligands have been described and their use for neurological and psychiatric diseases has been suggested (see, e.g., US 20040224953, WO2004089373, WO2004101546). $H_3$ receptor antagonists may be useful in treating various neuropsychiatric conditions, where cognitive deficits are an integral part of the disease, specifically ADHD, schizophrenia and Alzheimer's disease (see, for example, Hancock, A.; Fox, G. in *Drug Therapy* (ed. Buccafusco, J. J.). (Birkhauser, Basel, 2003).

Imidazole $H_3$ receptor antagonists are well known in the art. More recently, non-imidazole $H_3$ receptor antagonists have been disclosed in U.S. Pat. Nos. 6,720,328 and 6,849,621, and in US Published Applications 2004/0097483, 2004/0048843 and 2004/0019099. The present invention is a selection invention over US 2004/0097483.

SUMMARY OF THE INVENTION

The present invention provides the compound of formula I (I)

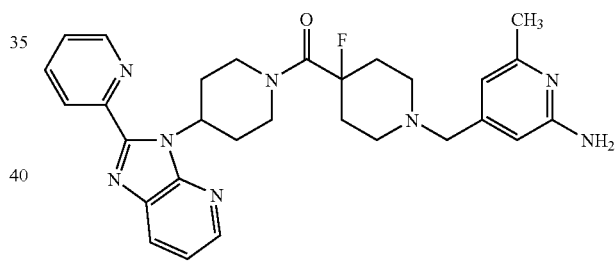

and pharmaceutically acceptable salts and solvates thereof.

The invention also provides a pharmaceutical composition comprising an effective amount of the compound of formula I and a pharmaceutically acceptable carrier.

The invention further provides methods for treating obesity, metabolic syndrome, diabetes, hepatic lipidosis or nonalcoholic fatty liver disease (each being a "Condition") comprising administering to a patient in need of such treatment an effective amount of a Compound of Formula I.

The invention further provides a pharmaceutical composition comprising an effective amount of a combination of the Compound of Formula I, at least one additional therapeutic agent, and a pharmaceutically acceptable carrier.

The invention further provides methods for treating a Condition comprising administering to a patient in need of such treatment: (i) an effective amount of the Compound of Formula I and (ii) at least one other additional therapeutic agent.

The invention also provides kits comprising a Compound of Formula I in a pharmaceutical composition, and one or more additional therapeutic agents in separate pharmaceutical compositions, wherein all of the separate pharmaceutical compositions are present in a single package.

DETAILED DESCRIPTION OF THE INVENTION

Definitions and Abbreviations

Figure 1:
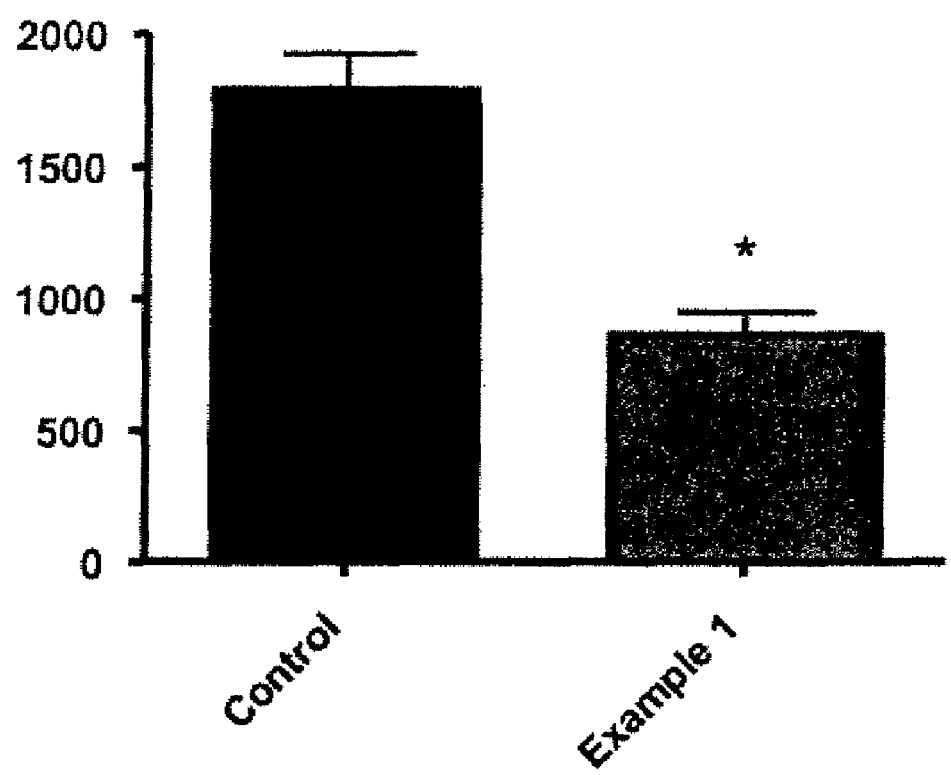
FIG. 1 shows the effect of the Compound of Formula I on triglyceride levels in obese mice. The black bar on the left represents control mice (i.e., vehicle-treated mice) and the grey bar on the right represents mice treated with the Compound of Formula I (10 mg/kg/day for 12 days administered via gavage). The y-axis represents liver triglyceride levels in mg/liver.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

"Patient" means a human or non-human mammal. In one embodiment a patient is a human. In another embodiment, a patient is a non-human mammal. In yet another embodiment, a patient is a companion animal, including but not limited to, a dog, cat, rabbit, ferret or horse. In a specific embodiment, a patient is a dog. In another specific embodiment, a patient is a cat.

As used herein, the term "composition" is intended to encompass a product comprising the specified ingredients in the specified amounts, as well as any product which results, directly or indirectly, from combination of the specified ingredients in the specified amounts.

Solvates of the Compound of Formula I are also contemplated herein. "Solvate" means a physical association of a compound of this invention with one or more solvent molecules. This physical association may involve varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Compound of Formula I can form salts which are also within the scope of this invention. Reference to the Compound of Formula I herein is understood to include reference to salts thereof, unless otherwise indicated. The term "salt(s)", as employed herein, denotes acidic salts formed with inorganic and/or organic acids with some or all of the basic moieties of the Compound of formula I, such as pyridine, benzimidazole, piperidine and aminopyridine. In one embodiment, a salt of the Compound of Formula I is a Pharmaceutically Acceptable Salt (i.e., non-toxic, physiologically acceptable). Salts of the Compound of the Formula I may be formed, for example, by reacting the Compound of Formula I with an amount of acid, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

All such salts are intended to be pharmaceutically acceptable salts within the scope of the invention and all acid and base salts are considered equivalent to the free forms of the corresponding compounds for purposes of the invention.

The Compound of Formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the Compound of Formula I (including those of the salts, solvates and prodrugs of the compound as well as the salts and solvates of the prodrugs), such as enantiomeric forms (which may exist even in the absence of asymmetric carbons), rotameric forms, atropisomers, and diastereomeric forms, are contemplated within the scope of this invention, individual stereoisomers of the Compound of Formula I may, for example, be substantially free of other isomers, or may be admixed, for example, as racemates or with all other, or other selected, stereoisomers. The use of the terms "salt", "solvate", "prodrug" and the like, is intended to equally apply to the salt, solvate and prodrug of enantiomers, stereoisomers, rotamers, tautomers, racemates or prodrugs of the inventive compound.

Polymorphic forms of the Compound of Formula I, and of the salts and solvates of the Compound of Formula I, are intended to be included in the present invention.

The term "metabolic syndrome" refers to a combination of risk factors for cardiovascular disease (CVD) identified in the National Cholesterol Education Program's Adult Treatment Panel III report. See for example the discussion by Grundy et al in *Circulation*, 109 (2004), 433-438. The components of metabolic syndrome are: 1) abdominal obesity; 2) atherogenic dyslipidemia; 3) raised blood pressure; 4) insulin resistance; 5) proinflamatory state; and 6) prothrombotic state.

The term "nonalcoholic fatty liver disease" or "NAFLD" describes a spectrum of liver diseases ranging from simple fatty liver (steatosis) to nonalcoholic steatohepatitis (ASH) with progressive fibrosis and liver failure. Hyperglycemia with or without evidence of hyperlipidemia is commonly associated with NAFLD. The disease exhibits the histological features of alcohol-induced liver disease in patients who do not consume significant amounts of alcohol. All of the stages of NAFLD have in common the accumulation of fat in the liver cells. Farrell and Larter in *Hepatology*, 243: S99-S112 (2006) describe NASH as "the lynchpin" between hepatic steatosis and cirrhosis in the spectrum of NAFLD. See also, Palekar, et al., *Liver Int.*, 26(2):151-6 (2006). In NASH, the fat accumulation of associated with varying degrees of inflammation and fibrosis. Conditions most commonly associated with NAFLD are obesity, type II diabetes and metabolic syndrome.

The terms "combination therapy" or "therapeutic combination" means the administration of the Compound of Formula I and one or more additional therapeutic agents useful for treating a Condition. The combinations and treatments of the present invention can be administered by any suitable means which produce contact of these compounds with the site of action in the body, for example in the plasma, liver or small intestine of a subject (mammal or human or other animal). Such administration includes coadministration of these therapeutic agents in a substantially simultaneous manner such as in a single tablet or capsule having a fixed ratio of active ingredients or in multiple, separate capsules for each therapeutic agent. Also, such administration includes use of each type of therapeutic agent in a sequential manner. In either case, the treatment using the combination therapy will provide beneficial effects in treating the condition. A potential advantage of the combination therapy disclosed herein may be a reduction in the required amount of an individual therapeutic compound or the overall total amount of therapeutic compounds that are effective in treating the condition. By using a combination of therapeutic agents, the side effects of the individual compounds can be reduced as compared to a monotherapy, which can improve patient compliance. Also, therapeutic agents can be selected to provide a broader range of complimentary effects or complimentary modes of action. The agents administered as combination therapy can act additively or synergistically. In one embodiment, the combination therapies of the invention comprise the administration of the Compound of Formula I and one additional therapeutic agent. In another embodiment, the combination therapies of the invention comprise the administration of the Compound of Formula I and two additional therapeutic agents.

As used herein, the term "cholesterol lowering agent" means any compound capable of lowering the cholesterol level in patient.

The term "$H_3$ receptor antagonist/inverse agonist" refers to any compound that acts as an antagonist or an inverse agonist to an $H_3$ receptor in a patient.

The term "weight loss agent" refers to any compound capable of causing a decrease in the weight of a patient.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a mammal or human.

The following abbreviations have the stated meanings: BOC is tert-butoxycarbonyl; Ac is acetyl; Bu is butyl; conc. is concentrated; DMF is N,N-dimethylformamide; EDCI is 1-(3-dimethylaminopropyl)-3-ethyl-carbodiimide hydrochloride; Et is ethyl; EtOAc is ethyl acetate; EtOH is ethanol; HOBt is hydroxybenzotriazole; HPLC is high performance liquid chromatography; Me is methyl; MeOH is methanol; $NaBH(OAc)_3$ is sodium triacetoxyborohydride; Pr is propyl; i-PrOH is isopropanol; TFA is trifluoroacetic acid; and THF is tetrahydrofuran.

Uses of the Compound of Formula I

The Compound of Formula I and pharmaceutically acceptable salts and solvates thereof are useful for treating a Condition in a patient.

Accordingly, in one embodiment, the invention provides a method for treating a Condition in a patient, comprising administering to the patient an effective amount of the Compound of Formula I.

In one embodiment, the Condition being treated is obesity.

In another embodiment, the Condition being treated is metabolic syndrome.

In another embodiment, the Condition being treated is nonalcoholic fatty liver disease.

In still another embodiment, the Condition being treated is diabetes. In one embodiment, the diabetes is Type I diabetes. In another embodiment, the diabetes is Type II diabetes.

In a further embodiment, the Condition being treated is hepatic lipidosis.

Other Therapeutic Agents

The combination therapies of the present invention comprise the administration of the Compound of Formula I and one or more additional therapeutic agents useful for treating a Condition.

Accordingly, in one embodiment, the invention provides a method for for treating a Condition in a patient, comprising administering to the patient: (i) an effective amount of the Compound of Formula I; and (ii) one or more additional therapeutic agents.

Additional therapeutic agents useful in the present methods include, but are not limited to cholesterol lowering agents, weight loss agents, antidiabetic agents and $H_3$ receptor antagonist/inverse agonists.

In one embodiment, the additional therapeutic agent is a cholesterol-lowering agent.

In another embodiment, the additional therapeutic agent is a weight loss agent.

In another embodiment, the additional therapeutic agent is an $H_3$ receptor antagonist/inverse agonist.

In still another embodiment, the additional therapeutic agent is an antidiabetic agent.

Cholesterol lowering agents useful in the combination therapies of the present invention, include but are not limited to: cholesterol biosynthesis inhibitors; bile acid sequestrants; sterol absorption inhibitors; 5-α-stanol absorption inhibitors; nicotinic acid and/or nicotinic acid receptor agonists; agonists or activators of peroxisome proliferators-activated receptors (PPAR); ileal bile acid transport ("IBAT") inhibitors (or apical sodium co-dependent bile acid transport ("ASBT") inhibitors; nicotinic acid (niacin) and/or nicotinic acid receptor agonists; acylCoA:cholesterol O-acyltransferase ("ACAT") inhibitors; cholesteryl ester transfer protein ("CETP") inhibitors; probucol or derivatives thereof, low-density lipoprotein ("LDL") receptor activators; omega 3 fatty acids ("3-PUFA"); natural water soluble fibers; plant sterols, plant stanols and/or fatty acid esters of plant stanols.

Non-limiting examples of suitable bile acid sequestrants include cholestyramine (a styrene-divinylbenzene copolymer containing quaternary ammonium cationic groups capable of binding bile acids, such as QUESTRAN® or QUESTRAN LIGHT® cholestamine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

Non-limiting examples of suitable cholesterol biosynthesis inhibitors include inhibitors of HMG-CoA reductase, squalene synthase inhibitors, squalene epoxidase inhibitors and mixtures thereof.

Non-limiting examples of suitable HMG-CoA reductase inhibitors include statins such as lovastatin (for example MEVACOR® which is available from Merck & Co.), pravastatin (for example PRAVACHOL® which is available from Bristol Meyers Squibb), fluvastatin, simvastatin (for example ZOCOR® which is available from Merck & Co.), atorvastatin, cerivastatin, CI-981, resuvastatin, rivastatin and pitavastatin (such as NK-104 of Negma Kowa of Japan), rosuvastatin; HMG-CoA reductase inhibitors, for example L-659,699 ((E,E)-11-[3'R-(hydroxyl-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride) and other sterol biosynthesis inhibitors such as DMP-565. In one embodiment, an HMG-CoA reductase inhibitor is selected from the group consisting of lovastatin, pravastatin fluvastatin, simvastatin, atorvastatin, cerivastatin, pitavastatin, and rosuvastatin. In another embodiment, the HMG-CoA reductase inhibitor is lovastatin, pravastatin and simvastatin. In another embodiment, a suitable HMG-CoA reductase inhibitor is simvastatin.

Weight loss agents useful in the combination therapies of the present invention include appetite suppressants, metabolic rate enhancers and nutrient absorption inhibitors. Appetite suppressant agents useful for treating a Condition include cannabinoid receptor 1 ($CB_1$) antagonists or inverse agonists (e.g., rimonabant); Neuropeptide Y (NPY1, NPY2, NPY4 and NTY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl] pyridine); melanin-concentrating hormone receptor (MCH1R and MCH2R) antagonists; melanocortin receptor agonists (e.g, Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); glirelin antagonists; leptin or derivatives thereof, opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagons-like peptide 1 (GLP-1) agonists; topiramate; and phytopharm compound 57. Metabolic rate enhancers include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone β agonists; uncoupling protein activators (UCP-1,2 or 3) (e.g., phytanic acid, 4-[(E)-2-(5,6,7,8-tetramethyl-2-naphtbalenyl)-1-propenyl]benzoic acid and retinoic acid); acyl-estrogens (e.g., oleoyl-estrone); glucocorticoid antagonists; 11-beta hydroxyl steroid dehydrogenase type 1 (11β HSD-1) inhibitors; melanocortin-3 receptor (Mc3r) agonists; and stearoyl-CoA desaturase-1 (SCD-1) compounds. Nutrient absorption inhibitors include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Cholesterol absorption inhibitors useful in the combination therapies of the present invention include, but are not limited to, ezetimibe.

Other additional therapeutic agents useful in the combination therapies of the present invention include, but are not limited to, rimonabant, phentermine, 2-methyl-6-(phenylethynyl)-pyridine, 3[(2-methyl-1,4-thiazol-4-yl)ethynyl]pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamnide, rolipram, cilomilast, phytanic acid, 4-[(E)-2-(5,6,7,8-tetramnethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

Examples of antidiabetic agents useful in the present methods for treating Type II diabetes include sulfonylureas, insulin sensitizers (such as PPAR agonists, DPPFV inhibitors, PTP-1B inhibitors and glucokinase activators), β-glucosidase inhibitors, insulin secretagogues, hepatic glucose output lowering compounds, and insulin.

Non-limiting examples of useful sulfonylurea drugs include glipizide, tolbutamide, glyburide, glimepiride, chlorpropamide, acetohexamide, gliamilide, gliclazide, glibenclamide and tolazamide. Insulin sensitizers include PPAR-γ agonists described in detail above, preferably troglitazone, rosiglitazone, pioglitazone and englitazone; biguanidines such as metformin and phenformin; DPPIV inhibitors such as sitagliptin, saxagliptin, denagliptin and vildagliptin; PTP-1B inhibitors; and glucokinase activators. β-Glucosidase inhibitors that can be useful in treating type II diabetes include miglitol, acarbose, and voglibose. Hepatic glucose output lowering drugs include Glucophage and Glucophage XR. Insulin secretagogues include sulfonylurea and non-sulfonylurea drugs such as GLP-1, exendin, GIP, secretin, glipizide, chlorpropamide, nateglinide, meglitinide, glibenclamide, repaglinide and glimepiride. Insulin includes all formualtions of insulin, including long acting and short acting forms of insulin.

The Compound of Formula I may be administered in combination with weight-loss agents for the treatment of diabetes. Examples of weight-loss agents useful in the present methods for treating diabetes include those listed above herein.

For treating diabetes, compounds of the invention may also be administered in combination with antihypertensive agents, for example β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

Certain meglitinide drugs lower blood glucose levels by stimulating the release of insulin from the pancreas. This action is dependent upon functioning β cells in the pancreatic islets. Insulin release is glucose-dependent and diminishes at low glucose concentrations. The meglitinide drugs close ATP-dependent potassium channels in the β cell membrane by binding at characterizable sites. This potassium channel blockade depolarizes the β cell, which leads to an opening of calcium channels. The resulting increased calcium influx induces insulin secretion. Non-limiting examples of suitable meglitinide drugs useful in the present methods include repaglinide and nateglinide.

Non-limiting examples of suitable antidiabetic agents that sensitize the body to the insulin that is already present include certain biguanides and certain glitazones or thiazolidinediones. Certain suitable biguanides lower blood sugar by decreasing hepatic glucose production, decreasing intestinal absorption of glucose and improving insulin sensitivity (increasing peripheral glucose uptake and utilization). A non-limiting example of a suitable biganide is metformin. Non-limiting examples of metformin include metformin hydrochloride (N,N-dimethylimidodicarbonimidic diamide hydrochloride, such as GLUCOPHAGE® Tablets from Bristol-Myers Squibb); metformin hydrochloride with glyburide, such as GLUCOVANCE™ Tablets from Bristol-Myers Squibb); buformin.

Non-limiting examples of antidiabetic agents that slow or block the breakdown of starches and certain sugars and are suitable for use in the compositions of the present invention include alpha-glucosidase inhibitors and certain peptides for increasing insulin production, Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of additional antidiabetic agents include orally administrable insulin. Non-limiting examples of suitable orally administrable insulin or insulin containing compositions include AL-401 from AutoImmune, and certain compositions as disclosed in U.S. Pat. Nos. 4,579,730; 4,849, 405; 4,963,526; 5,642,868; 5,763,396; 5,824,638; 5,843,866; 6,153,632; 6,191,105; and International Publication No. WO 85/05029 (each of which is incorporated herein by reference).

The present methods for treating NAFLD, include combination therapy comprising the administration of the Compound of Formula I and at least one $H_3$ receptor antagonist/inverse agonist. $H_3$ receptor antagonists/inverse agonists are well-known in the art. $H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation. $H_3$ receptor antagonists/inverse agonists are known to treat: allergy, allergy-induced airway (e.g., upper airway) responses, congestion (e.g., nasal congestion), hypotension, cardiovascular disease, diseases of the GI tract, hyper and hypo motility and acidic secretion of the gastro-intestinal tract, obesity, sleeping disorders (e.g., hypersomnia, somnolence, and narcolepsy), disturbances of the central nervous system, attention deficit hyperactivity disorder (ADHD), hypo and hyperactivity of the central nervous system (for example, agitation and depression), and/or other CNS disorders (such as Alzheimer's, schizophrenia, and migraine) in a patient such as a mammal. These compounds are particularly useful for treating allergy, allergy-induced airway responses and/or congestion.

$H_3$ receptor antagonist/inverse agonists useful in the combination therapies of the present invention include, but are not limited to, imidazole type, such as those described in International Publication Nos. WO 95/14007 and WO 99/24405; non-imidazole $H_3$ receptor antagonists described in U.S. Pat. No. 6,720,328; indole derivatives described in U.S. Publication No. US 2004/0019099; benzimidazole derivatives described in U.S. Publication No. US 2004/0048843A1 and U.S. Publication No. US 2004/0097483A1; and piperidine compounds described in U.S. Pat. No. 6,849,621. The above-listed patents and applications relating to $H_3$ antagonists/inverse agonists are incorporated herein by reference.

In one embodiment, the invention provides a method for treating NAFLD in a patient, comprising administering: (i) an effective amount of a Compound of Formula I, (ii) an HMG-CoA reductase inhibitor, and (iii) a bile acid sequestrant.

In another embodiment, the invention provides a method for treating NAFLD in a patient, comprising administering: (i) an effective amount of a Compound of Formula I, (ii) an HMG-CoA reductase inhibitor, and (iii) a weight loss agent.

In another embodiment, the invention provides a method for treating NAFLD in a patient, comprising administering: (i) an effective amount of a Compound of Formula I, (ii) an HMG-CoA reductase inhibitor, and (iii) a PPAR activator.

In still another embodiment, the invention provides a method for treating NAFLD in a patient, comprising administering: (i) an effective amount of a Compound of Formula I, (ii) an HMG-CoA reductase inhibitor, and (iii) a sterol absorption inhibitor.

In yet another embodiment, the invention provides a method for treating NAFLD in a patient, comprising administering: (i) an effective amount of a Compound of Formula I, (ii) an HEMG-CoA reductase inhibitor, and (iii) a 5-α-stanol absorption inhibitor.

In a further embodiment, the invention provides a method for treating NAFLD in a patient, comprising administering: (i) an effective amount of a Compound of Formula I, (ii) an HMG-CoA reductase inhibitor, and (iii) a cholesterol absorption inhibitor.

In another embodiment, the invention provides a method for treating NAFLD in a patient, comprising administering: (i) an effective amount of a Compound of Formula I, (ii) an HMC-CoA reductase inhibitor, and (iii) a $H_3$ receptor antagonist/inverse agonist.

In one embodiment, the invention provides a method for treating obesity in a patient, comprising administering: (i) an effective amount of a Compound of Formula I, and (ii) a weight loss agent.

In another embodiment, the invention provides a method for treating metabolic syndrome in a patient, comprising administering. (i) an effective amount of a Compound of Formula I, and (ii) a weight loss agent.

In another embodiment, the invention provides a method for treating diabetes in a patient, comprising administering: (i) an effective amount of a Compound of Formula I, and (ii) an antidiabetic agent.

In another embodiment, the invention provides a method for treating diabetes in a patient, comprising administering: (i) an effective amount of a Compound of Formula I and (ii) a weight loss agent.

Compositions and Administration

For preparing pharmaceutical compositions from the compound of this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Wiliams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid from preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the compound is administered orally.

In another embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg. In one embodiment, quantity of active compound in a unit dose of preparation is from about 1 mg to about 75 mg. In another embodiment, quantity of active compound in a unit dose of preparation is from about about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharnaceutically acceptable salts thereof will be regulated according to the judgnent of the attending clinician considering such factors as age, condition and size of the patient as well as seventy of the symptoms being treated. A typical recommended daily dosage regimen for oral administration can range from about 1 mg/day to about 300 mg/day. In one embodiment, a daily oral dosage is from about 1 mg/day to 75 mg/day, in two to four divided doses.

Similarly, when the invention comprises a combination of the compound of this invention and another therapeutic agent for treating a Condition, the two active components may be co-administered simultaneously or sequentially, or a single pharmaceutical composition comprising the compound of this invention and another compound in a pharmaceutically acceptable carrier can be administered. The components of the combination can be administered individually or together in any conventional dosage form such as capsule, tablet, powder, cachet, suspension, solution, suppository, nasal spray, etc. In one embodiment, the dose of the other therapeutic agent ranges from about 1 mg to about 1000 mg per dose. The exact dose, however, is determined by published material or by the attending clinician and is dependent on such factors as the potency of the compound administered, the age, weight, condition and response of the patient.

In various embodiments, non-limiting dosage ranges for selected other therapeutic agents useful in the present methods are set forth below. The exact dose, however, is determined by published material or by the attending clinician and is dependent on such factors as the potency of the compound administered, the age, weight, condition and response of the patient.

In one embodiment, a total daily dosage of cholesterol biosynthesis inhibitor(s) can range from about 0.1 to about 160 mg per day. In one embodiment, the dosage is from about 0.2 to about 80 mg/day, administered in a single dose or in 2-3 divided doses.

In another embodiment, a total daily dosage of peroxisome proliferator-activated receptor(s) activator(s) can range from about 50 to about 3000 mg per day. In one embodiment, the daily dose is from about 50 to about 2000 mg per day, administered in a single dose or in 2-4 divided doses.

In another embodiment, a total daily dosage of IBAT inhibitor(s) can range from about 0.01 to about 1000 mg/day. In one embodiment, the dosage is from about 0.1 to about 50 mg/day, administered in a single dose or in 2-4 divided doses.

In yet another embodiment, a total daily dosage of nicotinic acid can range from about 500 to about 10,000 mg/day. In one embodiment, the dosage is from about 1000 to about 8000 mg/day. In another embodiment, the dosage is from about 3000 to about 6000 mg/day, administered in a single dose or in divided doses. Generally, the total daily dosage of a NAR agonist can range from about 1 to about 100 mg/day.

In further embodiment, a total daily dosage of ACAT inhibitor(s) can range from about 0.1 to about 1000 mg/day, administered in a single dose or in 2-4 divided doses.

In another embodiment, a total daily dosage of CETP inhibitor(s) can range from about 0.01 to about 1000 mg/day, and preferably about 0.5 to about 20 mg/kg/day, administered in a single dose or in 2 or more divided doses.

In one embodiment, a total daily dosage of probucol or derivatives thereof can range from about 10 to about 2000 mg/day. In one embodiment, the dosage is from about 500 to about 1500 mg/day, administered in a single dose or in 2-4 divided doses.

In another embodiment, a total daily dosage of LDL receptor activator(s) can range from about 1 to about 1000 mg/day, administered in a single dose or in 2-4 divided doses.

In another embodiment, a total daily dosage of fish oil or Omega 3 fatty acids can range from about 1 to about 30 grams per day, administered in a single dose or in 2-4 divided doses.

In still another embodiment, a total daily dosage of natural water soluble fibers can range from about 0.1 to about 10 grams per day, administered in a single dose or in 2-4 divided doses.

In another embodiment, a total daily dosage of plant sterols, plant stanols and/or fatty acid esters of plant stanols can range from about 0.5 to about 20 grams per day, administered in a single dose or in 2-4 divided doses.

In a further embodiment, the total daily dosage of antidiabetic agents can range from about 1 to about 3000 mg per day. In one embodiment, the total daily dose ranges from about 50 to about 2000 mg per day, administered in a single dose or in 2-4 divided doses.

When separate pharmaceutical compositions comprising a compound of this invention and another compound for treating a Condition are to be administered, they can be provided in a kit comprising a single package, wherein the single package comprises a first container containing the Compound of Formula I and a pharmaceutically acceptable carrier, and one or more additional separate containers, wherein each separate container contains an additional therapeutic agent and a pharmaceutically acceptable carrier, with the compounds and agents being present in amounts such that the combination is therapeutically effective. A kit is advantageous for administering a therapeutic combination when, for example, the components of the therapeutic combination must be administered at different time intervals or when they are in different dosage forms.

EXAMPLES

General Methods

All solvents and reagents were used as received. Proton NMR spectra were obtained using a Bruker AV 500 (500 MHz) instrument and were reported as parts per million (ppm) downfield from Me₄Si. LCMS analysis was performed using an Applied Biosystems API-100 mass spectrometer equipped with a Shimadzu SCL-10A LC column: Altech platinum C18, 3 um, 33 mm×7 mm ID; gradient flow: 0 min, 10% CH₃CN; 5 min, 95% CH₃CN; 7 min, 95% CH₃CN; 7.5 min, 10% CH₃CN; 9 min, stop. Flash column chromatography was performed using Selecto Scientific flash silica gel, 32-63 mesh. Analytical and preparative TLC was performed using Analtech Silica gel GF plates. Chiral HPLC was performed using a Varian PrepStar system equipped with a Chiralpak OD colunm (Chiral Technologies).

Example 1

Preparation of the Compound of Formula I

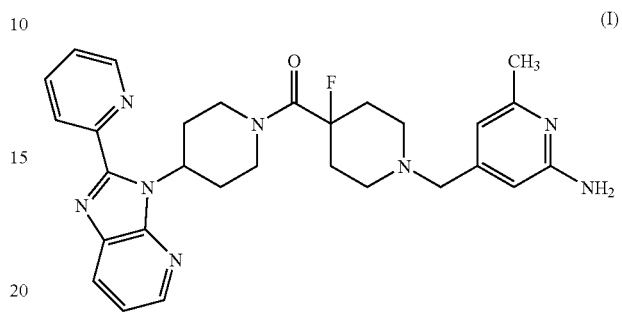

Step 1

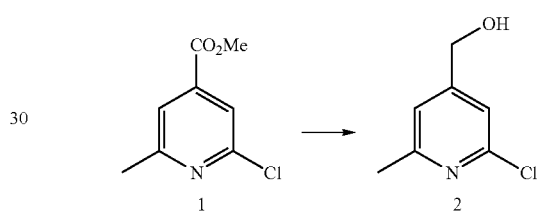

LiAlH₄ (10.0 g, 0.264 mol, 1.24 eq) was added portionwise to a solution of methyl-2-chloro-6-methylpyridine-4-carboxylate 1 (39.62 g, 0.213 mol) in dry Tf (800 mL) at room temperature with stirring over a period of 1.4 h. The resulting mixture was stirred for 1 h and quenched with water. 15% aqueous NaOH (100 mL) was added, followed by aqueous sodium-potassium tartrate (1 L). The resulting mixture was stirred for a further 1.25 h and extracted with dichloromethane (2×1 L) to give, after concentration, (2-chloro-6-methylpyridin-4-yl)-methanol 2 (31.06 g, 93%) as a yellow solid.

Step 2

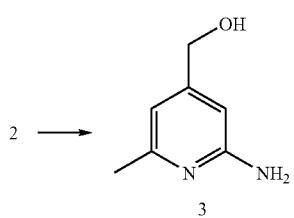

A bomb was charged with 2 (30.0 g, 0.190 mol) and aqueous conc NH₃ (225 mL) and the resulting mixture was heated at 210° C. for 20 h. The system was cooled to room temperature, the volatiles removed in vacito and the residue purified by column chromatography (dichloromethane: 0.4N NH₃ in MeOH 9:1) to give (2-aminio-6-methylpyridine-4-yl)-methanol as a mixture of free base and hydrochloride salt. The mixture was redissolved in dichloromethane:i-PrOH 1:1 (1

L) and treated with 20% aqueous NaOH (500 mL). The layers were separated and the organic phase extracted with dichloromethane:i-PrOH 1:1 (1×1 L). The combined organic phase was dried and the solvent evaporated to give (2-amino-6-methyl pyridine-4-yl)-methanol 3 (15.51 g, 59%) as pale orange crystals.

Step 3

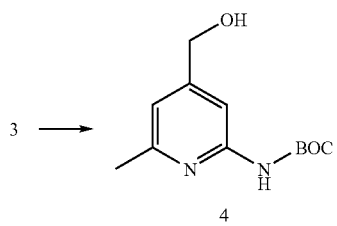

Di-tert-butyl dicarbonate (105.75 g, 0.485 mol, 4.33 eq) was added to a stirred solution of 3 (15.51 g, 0.112 mol) in tert-butyl alcohol (500 mL) at room temperature. The resulting mixture was heated at 95° C. for 19 h under a $N_2$ atmosphere, then cooled to room temperature and the solvent evaporated in vacuo. The resulting brown oil was purified by column chromatography (EtOAc:hexanes 1:1) to give the diprotected aminoalcohol (38.25 g) as a yellow solid. 25% aqueous NaOH (150 mL) was added to a solution of the above material in MeOH (500 mL) over a period of 10 min. The resulting mixture was stirred for 1 h, diluted with water (200 mL) and extracted with dichloromethane (2×750 mL) to give (4-hydroxymethyl-6-methyl-pyidine-2-yl)-carbamic acid tert-butyl ester 4 (21.0 g, 79% over two steps) as an orange foam.

Step 4

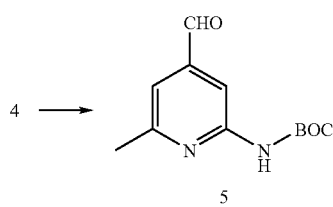

Dess-Martin periodinane (50.0 g, 0.118 mol, 1.34 eq) was portionwise added to a solution of 4 (21.0 g, 0.088 mol) in dichloromethane:pyridine 10:1 (1.1 L). The resulting solution was stirred at room temperature for 2 h and then water (700 mL) was added. The mixture was stirred for a further 5 min, and then the layers were separated. The aqueous layer was extracted with dichloromethane (1×1 l), the combined organic phase dried and the solvent evaporated to give a brown solid which was purified by column chromatography (EtOAc:hexane 1:2) to afford (4-formyl-6-methyl-pyridine-2-yl)-carbamic acid tert-butyl ester 5 (20.5 g, 99%) as a pale orange solid.

Step 5

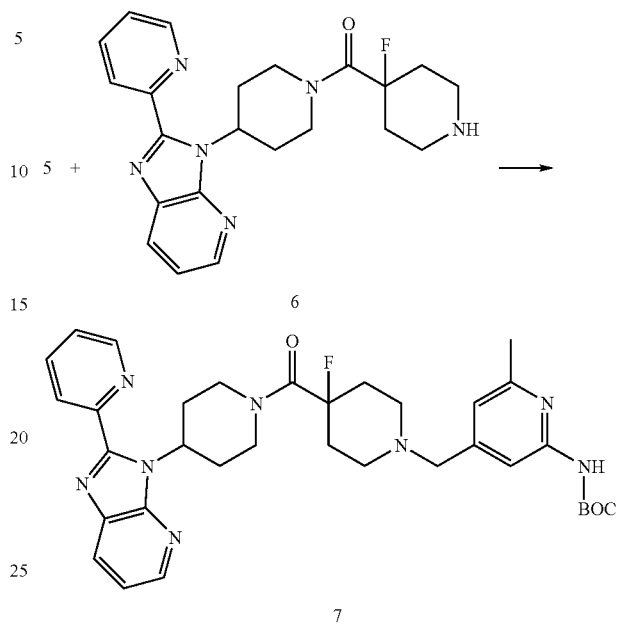

NaBH(OAc)$_3$ (57.8 g, 0.274 mol, 1.6 eq) was added to a solution of piperidine 6 (69.97 g, 0.171 mol, prepared using the method described in Example 2, below) and 5 (52.6 g, 0.223 mol, 1.3 eq in dry dichloromethane (5.4 L) at room temperature with stirring. The resulting mixture was stirred for 20 h and then washed with aqueous $K_2CO_3$. The layers were separated and the aqueous layer extracted with dichloromethane (1×2 L). The combined organic phase was dried and the solvent evaporated in vacuo to give an orange foam which was purified by column chromatography (dichloromethane: 0.4 N $NH_3$ in MeOH 95:5) to afford 7 (93.38 g, 54%) as a yellow foam.

Step 6

TFA (900 mL) was added to a solution of 7 (93.38 g, 0.149 mol) in dichloromethane (2.7 L). The resulting solution was stirred under a $N_2$ atmosphere for 26 h, then cooled to 0° C. and carefully basified with 15% aqueous ammonia solution. The layers were separated and the aqueous layer extracted with dichloromethane (1×1.5 L). The combined organic phase was dried and the solvent removed in vacuo to give a pale yellow solid which was triturated with dichloromethane (200 mL) and washed with diethyl ether (200 mL) to afford the Compound of Formula I (59.05 g, 75%) as a white solid. $^1$H NMR (500 MHz, CDCl$_3$, δ=7.29): 1.96-2.16 (m, 4H), 2.28-2.48 (m, 4H), 2.40 (s, 3H), 2.80 (m, 3H), 3.02-3.24 (m, 3H), 3.42 (s, 2H), 4.37 (s, 2H), 4.70 (m, 1H), 4.83 (m, 1H), 5.84 (m, 1H), 6.38 (s, 1H), 6.55 (s, 1H), 7.26 (dd, J=8.2, 4.7 Hz, 1H), 7.44 (ddd, J=7.5, 5.1, 1.2 Hz, 1H), 7.92 (app. td, J=<7.7>, 1.9 Hz, 1H), 8.09 (dd, J=8.0, 1.5 Hz, 1H), 8.32 (app. dt, J=8.0, <1.0> Hz, 1H), 8.40 (dd, J=4.7, 1.5 Hz), 8.74 (ddd, J=5.1, 1.9, 1.2 Hz, 1H). (C$_{29}$H$_{33}$FN$_8$O found M+H 529.3).

The preparation of the compound of Formula I can be realized in many ways known to those skilled in the art. While this example provides one particular method for preparing this compound; other procedures, for example those described in US 2004/0097483, are also applicable.

Example 2

Preparation of Intermediate Compound 6

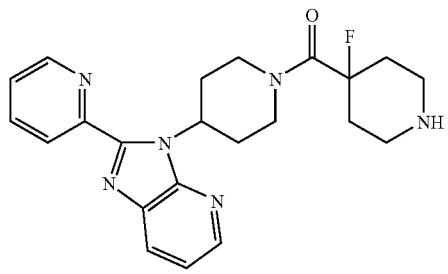

Step 1:

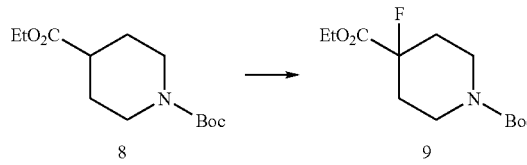

A solution of compound 8 (100 g, 0.389 mol) in THF (400 mL) was added dropwise over 1 h to a solution of lithium diisopropylamide (233 mL, 2.0 M in THF/heptane/ethylbenzene, 0.466 mol) in THF (300 mL) at 0° C. The red-orange solution was stirred at 0° C. for 30 min, and then transferred by cannula to a pre-cooled (0° C.) solution of N-fluorobenzenesulfonimide (153 g, 0.485 mol) in dry THF (600 mL). The reaction mixture was stirred at 0° C. for 30 min, and then at 20° C. for 18 h. The total solvent volume was reduced to approximately one third, and EtOAc (1 L) was added. The solution was washed successively with water, 0.1 N aqueous HCl, saturated aqueous NaHCO₃, and brine. The organic layer was dried over MgSO₄, filtered, and concentrated under reduced pressure to yield a crude liquid. Separation by flash chromatography (hexanes-EtOAc 6:1) gave compound 9 (93.5 g, 87%).

Step 2:

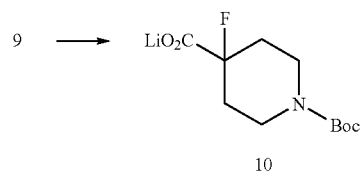

A solution of 9 (50 g, 0.181 mol) in THF (300 mL) and MeOH (200 mL) was treated with a solution of LiOH—H₂O (9.2 g, 0.218 mol) in water (100 mL) and then heated to 45° C. for 6 h. The mixture was then concentrated and dried in vacuo to provide 10 (45 g, 100%).

Step 3:

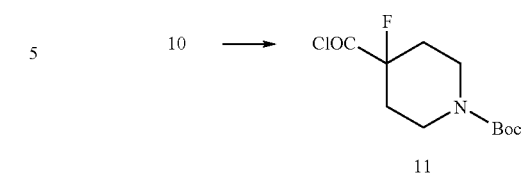

Compound 10 (20.4 g, 0.081 mol) was added slowly to a stirred flask of dichloromethane (250 mL) at 20° C. The resulting white slurry was cooled to 0° C. and treated slowly with oxalyl chlorde (6.7 mL, 0.075 mol) and a drop of DMF. After stirring at 20° C. for 0.5 h, e mixture was concentrated and dried in vacuo to provide 11.

Step 4A:

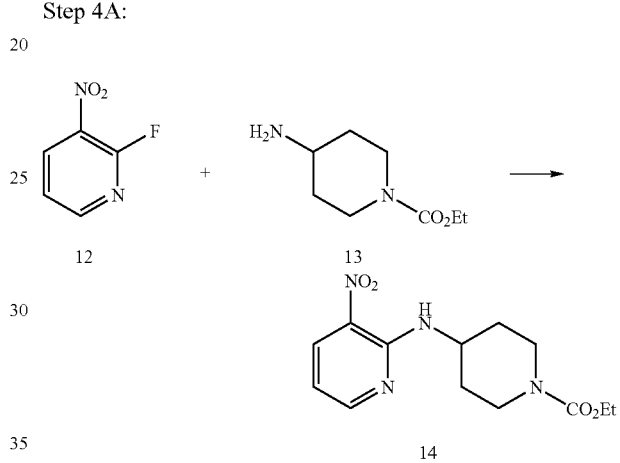

A mixture of 12 (64 g, 0.40 mol), 13 (84 mL, 0.52 mol), and K₂CO₃ (66 g, 0.48 mol) in anhydrous toluene (350 mL) was heated at reflux overnight. The reaction mixture was diluted with dichloromethane, washed three times with 5% aqueous NaOH, dried over Na₂SO₄, and concentrated. Recrystallization with MeOH provided 14 (121 g, 99%) as a yellow solid.

Step 4B:

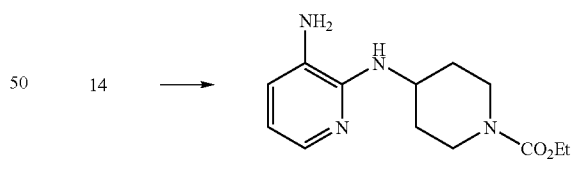

A suspension of 14 (121 g, 0.41 mol) and Raney Nickel (10 g) in EtOH (400 mL) was shaken under H₂ (40 psi) for 4 h. The mixture was filtered through a short pad of celite (washing with MeOH). The filtrate was concentrated and dried in vacuo to provide 15 (109 g, 99%) as a dark brown solid.

Step 4C:

-continued

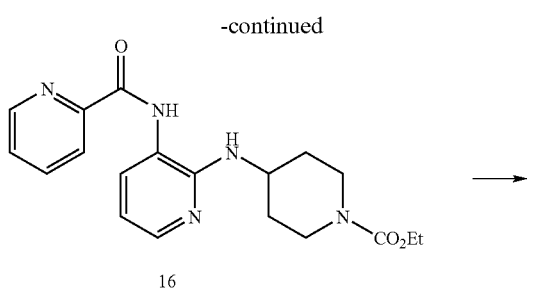

16

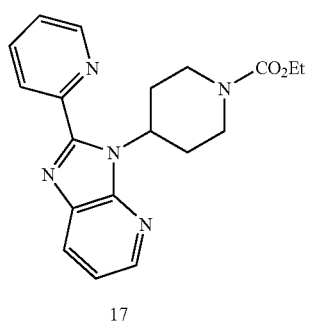

17

A solution of 15 (109 g, 0.41 mol) in dichloromethane: DMF 1:1 (500 mL) was treated with picolinic acid (61 g, 0.50 mol), EDCI (119 g, 0.62 mol), HOBt (84 g, 0.62 mol) and diisopropylethylamine (141 mL, 1.03 mol). The mixture was stirred at 70° C. for 6 h and then overnight at 20° C. The reaction mixture was diluted with EtOAc, washed 3 times with 5% aqueous NaOH, dried over $Na_2SO_4$, and concentrated. Flash chromatography (0-100% EtOAc/hexane) provided 16 (131 g, 86%).

Step 4D:

A solution of 16 (131 g, 0.36 mol) in acetic acid (200 mL) was heated at 120° C. overnight. The reaction mixture was cooled, carefully basified with 5% aqueous NaOH and extracted with $CH_2Cl_2$. The combined organic extracts were dried over $Na_2SO_4$ and concentrated. Flash chromatography (0-80% EtOAc/hexane) provided 17 (95 g, 76%) as a yellow solid.

Step 4E:

17 →

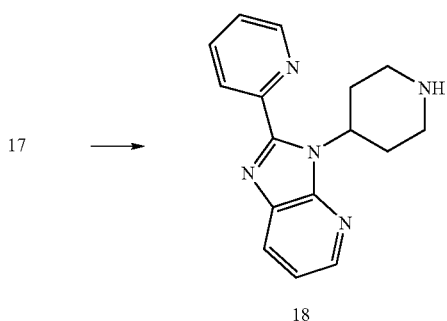

18

A solution of 17 (95 g, 0.27 mol) in anhydrous $CHCl_3$ (300 mL) was treated with iodotrimethylsilane (272 g, 1.36 mol) and heated at 70° C. for 5 h. The reaction mixture was cooled, quenched with cold 10% aqueous NaOH, and extracted with dichloromethane. The combined organic extracts were dried over $Na_2SO_4$ and concentrated. Flash chromatography (2N $NH_3$-MeOH/EtOAc) provided 18 (43 g, 57%) as a pale yellow solid.

Step 5:

A mixture of 18 (0.075 mol) in dichloromethane (250 mL) was treated with 11 (15 g, 0.054 mol) and diisopropylethylamine (25 mL, 0.135 mol) while maintaining a temperature of 20° C. After 1 h, the mixture was concentrated and then stirred in MeOH:dichloromethane:$H_2O$ (200 mL:200 mL:1 mL) for 1 h at 20° C. The solvent was then evaporated. Treatment with TFA (200 mL) in $CH_2Cl_2$ (250 mL) at 20° C. followed by flash chromatography (0-7% 7N $NH_3$—$CH_3OH$/$CH_2Cl_2$) provided 6 (80-90% from 10).

Example 3

Human $H_3$-Receptor Binding Assay

Binding assays were performed with membranes from HEK-293 cells stably expressing recombinant human histamine $H_3$ receptor. Each 200 µL assay volume contained 1.0 nM [$^3$H]$N^{-\alpha}$-methylhistamine, test compound, and 3 µg of membrane protein in 50 mM Tris-HCl, pH 7.4. Total binding was determined in the absence of compound and nonspecific binding in the presence of $10^{-5}$ M thioperamide. Material was incubated 30 minutes at 30° C. then filtered on GF/B filters. These were rinsed three times with cold buffer, then dried, impregnated with Meltilex scintillation counting medium, and counted. $K_i$ values were determined from standard curve-fitting procedures. For compounds generating less than 50% inhibition at the highest concentration tested, the percent inhibition at this concentration was recorded. Values are averages from two assays with duplicate determinations in each. Errors are expressed as the range of these values from the mean.

The compound of formula I has a $K_i$ of 4.6 nM in the recombinant human receptor assay.

Example 4

In Vitro Binding of the Compound of Formula I to Canine and Feline $H_3$ Receptors Binding assays were performed with membranes from a P2 pellet preparation of brain from each species as described in West et al., *Mol Pharmacol* 38:610-613 (1990). Frozen brains were thawed at room temperature and then disrupted in ten volumes (w:v) of ice-cold 50 mM Tris-HCl, pH 7.4, with a Polytron. Homogenates were centrifuged at 1000×g and supernatants then centrifuged at 50,000×g. Pellets from the second centrifugation were resuspended in buffer, sedimented again at 50,000×g, and stored frozen at −80° C.

Each 200 µL assay volume contained 1.0 nM [$^3$H]$N^{-\alpha}$-methylhlstamine, test compound, and 300 µg of membrane protein in 50 mM Tris-HCl, pH 7.4. Total binding was determined in the absence of compound and nonspecific binding in the presence of $10^{-5}$ M thioperamide. Assay mixtures are incubated 30 minutes at 30° C. then filtered on CF/B filters. Filters were rinsed three times with cold buffer, dried, impregnated with Meltilex scintillation counting medium, and counted. $IC_{50}$ values were determined using standard curve-fitting procedures and $K_i$ values were calculated from these using the method set forth in Cheng et al., *Biochem Pharmacol* 22:3099-3108 (1973). Each competition binding assay comprised ten concentrations of compound, each concentration assayed in duplicate. Binding data obtained for the Compound of Formula I to canine and feline $H_3$ receptors are set forth below in Table 1. Ki values are averages plus or minus the standard error of the mean from multiple assays as indicated.

TABLE 1

Binding of the Compound of Formula I to Canine and Feline $H_3$ Receptors

| Species | N | $K_i$ (nM) |
|---|---|---|
| Dog | 2 | 1.3 ± 0.2 |
| Cat | 3 | 4.9 ± 0.6 |

Example 5

Canine Pharmacokinetic Data for the Compound of Formula I

The Compound of Formula I was administered at a dose of 3 mg/kg to fasted beagle dogs orally (PO) at 3 mg/g (0.4% MC formulation) and i.v. at 3 mg/g (captisol, pH 5.1 fornulation). Blood samples were taken at multiple time intervals for 48 hours post dosing. The blood samples were converted to plasma and stored at −20° C. until being assayed for the Compound of Formula I using an HPLC-API-MS/MS procedure. The pharmacokinctic parameters that were calculated from thiis study are sumarized in Table 2 below. As shown in this table, the oral bioavailability of the Compound of Formula I in fasted dogs was 58%. The mean half-life after i.v. administration was 9.5 hr. The clearance was 1.7 mL/min/kg.

TABLE 2

Pharmacokinetic Parameters of the Compound of the Invention in Dogs after Oral (0.4% MC) and IV (captisol, pH 5.1) administration

| Parameter (units) | Oral (N = 3) | IV (N = 3) |
|---|---|---|
| Dose (mg/kg) | 3 | 3 |
| AUC (0-∞) (μg · hr/mL) | 18.9 | 32.8 |
| Bioavailability (%) | 58 | NA |
| Half-life (hr) | NA | 9.5 |
| Mean Residence Time (MRT) (hr) | 18.6 | 10.9 |
| Mean Absorption Time (MAT) ($MRT_{po} - MRT_{iv}$)(hr) | 7.8 | NA |
| Oral Cmax (μg/mL) | 0.91 | NA |
| Clearance (mL/min/kg) | NA | 1.7 |
| $V_d$ (ss) (L/kg) | NA | 1.1 |

NA = not available

Example 6

Diet-Induced Obesity in Mice

Diet-induced obesity (DIO) was determined according to the following procedure. Young mice were maintained in individual cages at 22° C. on a 12:12 hr light/dark cycle. Mice were made obese with a high fat diet. Mice were orally gavaged daily with vehicle or compound; body weight and food intake were monitored daily.

The Compound of Formula I showed statistically significant inhibition of weight gain in mice when administered orally once a day in 20% aqueous hydroxypropyl-β-cyclodextrin (HPBCD) at dose of 0.3 mg/kg. Compounds specifically disclosed in US 2004/0097483 typically have minimum efficacious dose of 3 mg/kg or higher.

Example 7

Effect of the Compound of Formula I on Liver Triglycerides in Obese Mice

The Compound of Formula I was administered daily for 12 days via gavage to mice having diet-induced obesity at a dosage of 10 mg/kg/day (vehicle 0.4% aqueous methylcellulose (MC); see procedure for diet-induced obesity described above).

On day 12, the animals were sacrificed, their livers were collected, and liver pieces were extracted according to the procedure of Folch et al., *J. Biol. Chem.* 226:497-509 (1957). The collected liver tissue was then homogenized in 6 mL of chloroform:methanol (2:1), 4 mL water was added to the homogenized mixture and the resulting solution was vortexed, then centrifuged at 1000×g for 30 minutes. The chloroform layer was removed and dried under nitrogen to provide the extracted lipids, which were redissolved in 1 mL chloroform and aliquots were transferred into HPLC sample vials. Samples were dried under nitrogen and redissolved in 1 mL hexane:isopropanol (98.8:1.2).

Chromatography was performed using an isocratic mobile phase containing 98.8% hexane and 1.2% isopropanol at a flow rate of 2 mL/min through a Zorbax Sil (4.6×25 cm) silica column (Agilent Technologies #880952-701). Lipids in a 5 μL injection were detected by absorbance at 206 nm and quantitated by computer integration (System Gold, Beckman) of elution profiles. Cholesterol, cholesteryl ester, and triglyceride concentrations were determined by comparison to standard curves using Non-polar Lipid Mix-B, Matreya, Inc., Pleasant Gap, Pa. cat. #1130.

The results, illustrated in FIG. 1, show that the Compound of Formula I caused statistically significant 52% reduction in liver triglycenrde content relative to control (average of 861±87 mg/liver in the compound treated group vs. 1789±135 mg/liver in the vehicle treated group).

Example 8

Assessment of Oral Tolerance of the Compound of Formula I in Dogs

Male and female beagle dogs (N=6, age≧4 months, each having a body weight of from 10-15 kg) were used in this study. The treated animals (N=4) were orally administered the Compound of formula I once a day for 7 days at a daily dosage of 5 mg/kg (5 times proposed efficacy dose). The control animals (N=2) were orally administered vehicle only. Animals were fasted for 8 hours prior to each administration of the Compound of formula I or vehicle and were fasted for 2 hours after each administration of the Compound of formula I or vehicle. Blood samples were collected before, during, and after the treatment period for pharmacokinetic analysis.

Collection of Plasma Samples

Approximately 4.0±1 mL of blood was drawn from each animal at prior to the study (day 0), at 24 hours after the first dose (day 1), and at the end of the study (day 7), using jugular venipuncture and immediately placed into separated Vacutainer® tubes containing EDTA anticoagulant, and processed for plasma. The plasma was aspirated and divided into two aliquots (≧0.3 ml each) and each aliquot was frozen at −70° C. or less.

Analysis of Plasma Samples

Collected blood plasma samples were analyzed for the concentration of the Compound of formula I using the following analytical method:

LC/MS Instrument:
Mass spectrometer: Finnegan (Thermoquest) Quantum
Ion source: APCI
Liquid Chromatograph: Shimadzu LC-10AD
Autosampler: LEAP Technologies HTS PAL
Computer. Gateway
Quantitative software: Xcalibur 2.0
Quantum Tuning Parameters:
Vaporizer temperature: 450° C.
Discharge current: 20v
Heated capillary temperature: 350° C.
Collision gas: Argon, 1.5 mTorr
Sheath gas pressure: Nitrogen, 49 psi
Aux. gas pressure: Nitrogen, 0 psi
MS/MS Scan Functions:

Compound Y

| Compound | Parent (m/z) | Product (m/z) | Collision Energy (eV) |
|---|---|---|---|
| Compound of formula I | 529.2 | 197 | 36 |
| Compound Y (Internal Standard) | 500.2 | 197 | 29 |

LC Conditions:
Mobile Phase:
A: 20/80% methanol:water, 10 mM ammonium acetate
B: 100% methanol
Flow Rate: 0.8 mL/min
Sample Processing Method:
A: Preparation of stock solution:
0.1, 1, 10, 100, 1000 ng/μL in 50:50 methanol:water (1000 in DMSO) for standards.
1, 10, 100 ng/μL in 50:50 methanol:water for QCs.
B: Plasma standard curve and QC preparation: stock solution spiked in matrix identical to samples.
Concentration of standard curve:
  0, 1, 2.5, 5, 10, 25, 50, 100, 250, 500, 1000, 2500, 5000, 10000, 25000 ng/mL.
Concentration of QCs:
  25, 250, 2500 ng/mL.

C: Internal Standard Solution: 0.1 ng/μL of Compound Y in acetonitrile.
D: Sample Preparation Procedure:
1) Pipette 40 μL of sample into a 1 mL 96-well plate.
2) Add 150 μL of internal standard solution to each well.
3) Gently vortex plate for 1 minute.
4) Centrifuge samples for 10 minutes (Eppendorf 5810 Centifuge).
5) Pipette 100 μL of supernatant into a 350 μL 96-well plate.

Results

Results of the above-described study are set forth below in Table 3:

TABLE 3

Blood Plasma Levels of the Compound of Formula I in Treated Animals

| Sex of animal | Plasma level at Day 0 (ng/mL) | Plasma level at Day 1 (ng/mL) | Plasma level at Day 7 (ng/mL) |
|---|---|---|---|
| male | 0 | 118 | 263 |
| male | 6.8 | 157 | 207 |
| female | 0 | 604 | 680 |
| female | 0 | 148 | 540 |
| Mean | 1.70 | 256.75 | 422.50 |

These results indicate that the Compound of formula I was accumulated 7 days after daily oral administration of this compound. Accumulation was more pronounced in female dogs compared to male dogs. The compound was well tolerated when administered daily at a dose of 5 mg/kg. No adverse events were observed during the study.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A method of treating obesity comprising administering to a patient in need of such treatment an effective amount of a compound having the structure:

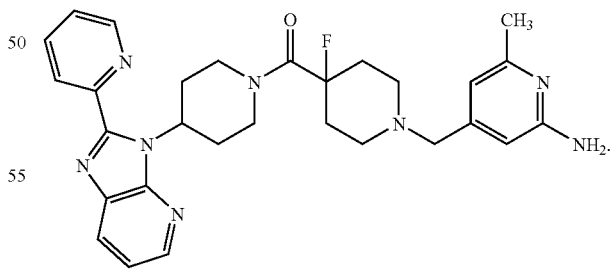

2. The method of claim 1, wherein the patient is a dog or a cat.

* * * * *